US006821990B2

(12) United States Patent
Kesseler

(10) Patent No.: US 6,821,990 B2
(45) Date of Patent: Nov. 23, 2004

(54) ETHANOL SOLVATE OF (-)-CIS-2-(2-CHLOROPHENYL)-5,7-DIHYDROXY-8 [4R-(3S-HYDROXY-1-M ETHYL) PIPERIDINYL]-4H-1-BENZOPYRAN-4-ONE

(75) Inventor: Kurt M. Kesseler, Hofheim (DE)

(73) Assignee: Aventis Pharma Deutschland GmbH, Frankfurt (DE)

(*) Notice: Subject to any disclaimer, the term of this patent is extended or adjusted under 35 U.S.C. 154(b) by 114 days.

(21) Appl. No.: 09/760,590

(22) Filed: Jan. 16, 2001

(65) Prior Publication Data

US 2001/0051638 A1 Dec. 13, 2001

Related U.S. Application Data

(60) Provisional application No. 60/287,593, filed on Jan. 18, 2000.

(51) Int. Cl.[7] ................. A61K 31/445; C07D 405/04
(52) U.S. Cl. ........................... 514/320; 546/197
(58) Field of Search ...................... 514/320; 546/197

(56) References Cited

U.S. PATENT DOCUMENTS

| | | | |
|---|---|---|---|
| 4,900,727 A | 2/1990 | Kattige et al. | 514/212 |
| 5,284,856 A | 2/1994 | Naik et al. | 514/320 |
| 5,908,934 A * | 6/1999 | Kim | 546/216 |
| 6,576,647 B2 * | 6/2003 | Bafus et al. | |

FOREIGN PATENT DOCUMENTS

EP 0366061 2/1990

OTHER PUBLICATIONS

Stadler et al. "Flavopiridol a novel cycli–dependent kinase . . . " CA 132;131947 (2000).*

Cheronis "Semimicro experimental organic chemistry" DeGratt p.32–35 (1958).*

Evans "An introduction to crystal chemistry" Cambredge press p.393–397 (1964).*

Li, Ping et al: "Evaluation of Intravenous Flavopiridol Formulations" PDA J. Phar. Sci. Technol. (1999), 53(3), 137–140.

Sedlacek et al.: "Flavopiridol, a New Kinase Inhibitor for Tumor Therapy", Int. J. Oncology, vol. 9, pp. 1143–1168.

* cited by examiner

*Primary Examiner*—Celia Chang
(74) *Attorney, Agent, or Firm*—Lawrence L. Martin; Balaram Gupta; Joseph Kirk

(57) ABSTRACT

An ethanol solvate form of (−)-cis-2-(2-chlorophenyl)-5,7-dihydroxy-8[4R-(3S-hydroxy-1-methyl)piperidinyl]-4H-1-benzopyran-4-one hydrochloride (Form II), a method of making Form II and a composition comprising Form II.

7 Claims, No Drawings

ETHANOL SOLVATE OF (-)-CIS-2-(2-CHLOROPHENYL)-5, 7-DIHYDROXY-8 [4R-(3S-HYDROXY-1-M ETHYL) PIPERIDINYL]-4H-1-BENZOPYRAN-4-ONE

This application claims the benefit of U.S. Provisional application No. 60/287,593, filed Jan. 18, 2000 now abandoned.

BACKGROUND OF THE INVENTION

The compound (−)-cis-2-(2-chlorophenyl)-5,7-dihydroxy-8[4R-(3S-hydroxy-1-methyl)piperidinyl]-4H-1-benzopyran-4-one or one of its pharmaceutically acceptable salt forms (known as "Flavopiridol") is an immunomodulator and antiinflammatory agent (U.S. Pat. No. 4,900,727), and inhibitor of oncogene-encoded kinases or growth factor receptor tyrosine kinases (U.S. Pat. No. 5,284,856). Flavopiridol is a strong inhibitor of cyclin dependent kinases (CDKs) including CDK1, CDK2, CDK4, CDK6 and CDK7, (cdk1/cyclin B; cdk2/cyclin A; cdk2/cyclin E; cdk4/cyclinD; cdk6/cyclinD; cdk7/cyclin H) with the potential to cause inhibition of cell cycle progression in $G_1$ and $G_2$ by multiple mechanisms relatable to cdk inhibition. See *International Journal of Oncology* 9:1143–1168 (1996). Also, Flavopiridol has been shown to inhibit the EGF receptor family, the receptor associated SRC family kinases, and signal transducing kinases. In vitro and in vivo experiments have shown that Flavopiridol is able to inhibit a broad type range of human tumors, leukemias and lymphomas.

(−)-cis-2-(2-chlorophenyl)-5,7-dihydroxy-8[4R-(3S-hydroxy-1-methyl)piperidinyl]-4H-1-benzopyran-4-one or a pharmaceutically acceptable salt thereof crystallizes into numerous solvates with solvents such as ethanol, DMSO, methanol, acetonitrile/isopropanol, ethanol/isopropanol, and isopropanol and solvate hydrates such as ethanol/ and isopropanol/water combinations. The superior solvate form is the Flavopiridol hydrochloride ethanol solvate form (hereafter "Form II").

The use of ethanol over the other solvents used to produce solvates presents advantages of less toxicity (e.g., methanol, isopropanol solvates).

A subject of the instant invention is Form II of (−)-cis-2-(2-chlorophenyl)-5,7-dihydroxy-8[4R-(3S-hydroxy-1-methyl)piperindinyl]-4H-1-benzopyran-4-one, this means the solvate of ethanol with (−)-cis-2-(2-chlorophenyl)-5,7-dihydroxy-8[4R-(3S-hydroxy-1-methyl)piperidinyl]-4H-1-benzopyran-4one hydrochloride. Said Form II can be described by x-ray powder diffraction in the following, obtained using Cu K-alpha radiation:

| D Space- Å |
|---|
| 12.763 |
| 6.389 |
| 3.194 |
| 13.244 |
| 4.259 | and more preferably as:

| D Space- Å |
|---|
| 12.763 |
| 6.389 |
| 3.194 |
| 13.244 |
| 4.259 |
| 12.036 |
| 2.824 |
| 8.659 |
| 6.012 |
| 5.397 |
| 3.447. |

Also, Form II is further identified as:

| D Space- Å | Relative Intensity |
|---|---|
| 12.763 | Strong |
| 6.389 | Medium |
| 3.194 | Weak |
| 13.244 | Weak |
| 4.259 | Weak |
| 12.036 | Weak |
| 2.824 | Weak |
| 8.659 | Weak |
| 6.012 | Weak |
| 5.397 | Weak |
| 3.447 | Weak |

Further, Form II may be identified as:

| D Space- Å | Relative Intensity (%) |
|---|---|
| 12.763 | 100.0 |
| 6.389 | 35.7 |
| 3.194 | 22.2 |
| 13.244 | 18.0 |
| 4.259 | 13.8 |
| 12.036 | 13.8 |
| 2.824 | 9.5 |
| 8.659 | 8.3 |
| 6.012 | 7.2 |
| 5.397 | 6.9 |
| 3.447 | 6.5 |

Form II may also be identified as in Table 1:

TABLE 1

| 2 Theta Angle (°) | D Space- Å | Relative Intensity | Relative Intensity (%) |
|---|---|---|---|
| 6.920 | 12.763 | Strong | 100.0 |
| 13.850 | 6.389 | Medium | 35.7 |
| 27.908 | 3.194 | Weak | 22.2 |
| 6.669 | 13.244 | Weak | 18.0 |
| 20.838 | 4.259 | Weak | 13.8 |
| 7.339 | 12.036 | Weak | 13.8 |
| 31.660 | 2.824 | Weak | 9.5 |
| 10.208 | 8.659 | Weak | 8.3 |
| 14.722 | 6.012 | Weak | 7.2 |
| 16.413 | 5.397 | Weak | 6.9 |
| 25.829 | 3.447 | Weak | 6.5 |

Form II can be used as a pharmaceutical, optionally together with pharmaceutically acceptable carriers and/or excipients. Furthermore, it can be used for the production of other polymorphs or pseudopolymorphs of (−)-cis-2-(2- chlorophenyl)-5,7-dihydroxy-8[4R-(3S-hydroxy-1-methyl) piperidinyl]-4H-1-benzopyran-4-one.

Form II is hygroscopic. It can be used in water free form or in a form with a certain water content. The use in a form, which is essentially free from water is preferred.

Another subject of the instant invention is a process for the production of Form II of (−)-cis-2-(2-chlorophenyl)-5, 7-dihydroxy-8[4R-(3S-hydroxy-1-methyl)piperidinyl]-4H-1-benzopyran-4-one.Steps of the production process of Form II of (−)-cis-2-(2-chlorphenyl)-5,7-dihydroxy-8[4R-(3S-hydroxy-1methyl)piperidinyl]4H-1-benzopyran-4-one are a) dissolving a sufficient amount of (−)-cis-2-(2-chlorophenyl)-5,7-dihydroxy-8[4R-(3S-hydroxy-1-methyl)piperidinyl]-4H-1-benzopyran-4one hydrochloride in a sufficient amount of ethanol thus forming a mixture, b) heating the mixture to about 50 to about 80° C.;

c) optionally filtering off undissolved material from the mixture thus forming a solution d) concentrating the solution until about 50 to about 90% of the volatiles are removed, e) cooling the solution, for example, to about 0 to 10° C. and optionally isolating (−)-cis-2-(2-chlorophenyl)-5, 7-dihydroxy-8[4R-(3S-hydroxy-1-methyl)piperidinyl]-4H-1-benzopyran-4-one hydrochloride crystals thus obtained; and f) optionally drying the crystals.

A "sufficient amount" of (−)-cis-2-(2-chlorophenyl)-5,7-dihydroxy-8[4R-(3S-hydroxy-1-methyl)piperidinyl]-4H-1-benzopyran-4one hydrochloride is that amount sufficient to be dissolved and heated according to the steps of the invention to form enough crystals to be recovered. Likewise, a "sufficient amount" of ethanol is that amount sufficient to dissolve at least a portion of the (−)-cis-2-(2-chlorophenyl)-5,7-dihydroxy-8[4R-(3S-hydroxy-1-methyl)piperidinyl]-4H-1-benzopyran-4one hydrochloride added thereto in order to dissolve a portion thereof. These amounts can be experimentally determined.

The "volatiles" are those agents which may be evaporated during heating such as ethanol and/or water.

The present invention also includes a pharmaceutical composition comprising a therapeutically effective amount of Form II and a pharmaceutically acceptable carrier.

A "pharmaceutically acceptable carrier" is an agent which is non-toxic, does not interfere with the therapeutic profile of Form II and is appropriate to the method of administration. Form II is preferably administered by the intravenous route over an appropriate period of time for cancer chemotherapy. Preferably, Form II is mixed with one or more pharmaceutically acceptable carriers. For example, Form II may be mixed with iso-osmotic and pH controlled liquids such as water, dextrose/water or saline/water for injection intravenously into the patient.

A "therapeutically effective amount" of Form II and will vary with the individual, concomitant therapy, the disease, and other variable factors. Typically, this amount will be about 0.001 mg/kg to 100 mg/kg per day.

Form II is useful as a protein kinase inhibitor and cyclin dependent kinase inhibitor, and is useful in the treatment for various forms of cancer.

SYNTHESIS

In step a) of the said production process one part of (−)-cis-2-(2-chlorophenyl)-5,7-dihydroxy-8[4R-(3S-hydroxy-1-methyl)piperidinyl]-4H-1-benzopyran-4-one is dissolved in 10 to 30, preferably 15 to 25 in particular 19 to 21 parts of ethanol. Preferably, ethanol which is essentially free from water is used. (−)-cis-2-(2-Chlorophenyl)-5,7-dihydroxy-8[4R-(3S-hydroxy-1-methyl)piperidinyl]-4H-1-benzopyran-4-one can be obtained as disclosed in U.S. Pat. No. 5,284,856; preferably, (−)-cis-2-(2-chlorophenyl)-5,7-dihydroxy-8[4R-(3S-hydroxy-1-methyl)piperidinyl]-4H-1-benzopyran-4-one is produced as outlined in Example 1 below.

The heating of the obtained mixture is carried out for preferably about one hour to 50 to 80, preferably 60 to 80, and in particular 70 to 79° C. If solid substance is observed in the solution, it can be filtered off, preferably while the solution is still hot.

The obtained solution is concentrated by methods known to a person skilled in the art, preferably by distillation under atmospheric or under reduced pressure. Concentration is carried out until 50 to 90%, preferably 55 to 85%, in particular 60 to 80% of the volatiles have been removed.

The remaining suspension is subsequently cooled, preferably to about 0 to 10° C. and the obtained crystals are removed from the suspension, preferably by filtration.

The obtained crystals can be dried, preferably under reduced pressure.

EXAMPLE 1

Synthesis of Form II

A reactor is charged under nitrogen atmosphere with (−)-cis-1-methyl-4R-(2,4,6-trimethoxyphenyl)-3S-piperidinol) and acetic anhydride. Boron trifluoride etherate is added at a constant rate while stirring and cooling the resulting solution to 8–20° C. After the addition is complete the resulting mixture is stirred at 20–30° C. for 3–5 hours. The reaction mixture is cooled to 8–12° C. and ice-water is added while stirring followed by addition of aqueous sodium hydroxide until pH 10–11 is attained. The mixture is extracted with ethyl acetate. The ethyl acetate extracts are pooled and concentrated under vacuum. The residue is taken up in methanol and water. Then sodium hydroxide (about 50% aqueous solution) is added. The reaction mixture is stirred at 20–30° C. for 2–3 hours. The mixture is evaporated under reduced pressure at ≦80° C. The residue is cooled to 15–20° C. and brought to pH 8.5–9.5 using concentrated hydrochloric acid. A solid precipitates, which is collected by filtration washed with demineralized water and dried under reduced pressure to give ((−)-cis-1-methyl-4-(3-acetyl-4,6-dimethoxy-2-hydroxy)phenyl-3-piperidinol).

((−)-cis-1-methyl-4-(3-acetyl-4,6-dimethoxy-2-hydroxy) phenyl-3-piperidinol) is then added portionwise to a stirred suspension of potassium tert. butoxide in dry N,N-dimethylforamide at such a rate that the temperature does not exceed 20° C. After the addition is complete the resulting mixture is stirred for one hour at ≦30° C. Methyl 2-chlorobenzoate is added at such a rate, that the temperature does not exceed 30° C. the resulting mixture is stirred at 20–30° C. for 4–6 hours. Demineralized water is added, followed by concentrated hydrochloric acid until the pH of the mixture reaches 6–8. The mixture is extracted two times using chloroform. The chloroform extracts are pooled together and concentrated under reduced pressure.

After cooling the remaining oil to ≦40° C., concentrated hydrochloric acid is added. The mixture is then stirred at ≦40° C. for ≦2 hours or overnight is necessary. After cooling the reaction mixture to 15–30° C., water and chloroform are added. The resulting mixture is basified to pH 8.5–10.5 using sodium hydroxide solution (50%). The phases are separated. The aqueous layer is then extracted with chloroform. The combined organic extracts are evaporated under reduced pressure to yield (−)-cis-2-(2-Chlorophenyl)-5,7-dimethoxy-8-[4R-(3S-hydroxy-1-methyl)-piperidinyl]-4H-1-benzopyran-4-one as an oil, which is directly used in the next step without purification.

To (−)-cis-2-(2-chlorophenyl)-5,7-dimethoxy-8-[4R-(3S-hydroxy-1-methyl)-piperidinyl]-4H-1benzopyran-4-one, quinoline and pyridine hydrochloride are added. The resulting mixture is heated to 160–190° C. while stirring. Stirring is continued while maintaining the temperature at 160–190° C. for 2 hours. After cooling the reaction mixture to 90–110° C. water is added. The resulting mixture is basified to pH 7.5–8.5 using saturated sodium carbonate solution, and extracted twice with a mixture of ethanol and chloroform. The combined extracts are evaporated to dryness to obtain (+)-cis-2-(2-chlorophenyl)-5,7-dihydroxy-8-[4R-(3S-hydroxy-1-methyl)piperidinyl]-4H-1-benzopyran-4-one crude as a brown gum, which is purified as follows.

To (+)-cis-2-(2-chlorophenyl)-5,7-dihydroxy-8-[4R-(3S-hydroxy-1-methyl)piperidinyl]-4H-1-benzopyran-4-one crude, acetone is added. The resulting mixture is stirred at 55–60° C. for 30–60 minute, then cooled to 15–20° C. and stirred for another 1–2 hours. The precipitated solid is isolated by filtration, washed twice with acetone and dried under reduced pressure to give (+)-cis-2-(2-chlorophenyl)-5,7-dihydroxy-8-[4R-(3S-hydroxy-1-methyl)piperidinyl]-4H-1-benzopyran-4-one in a purified form.

The free base from the previous step is suspended in ethanol and acidified using concentrated hydrochloric acid at such a rate that the temperature does not exceed 30° C. During this process initially all of the solid dissolves and then the hydrochloride precipitates. The suspension is cooled to 0–10° C. and stirred for 1 hour while maintaining the temperature. The crystals are isolated by filtration and washed with cold ethanol to yield (−)-cis-2-(2-chlorophenyl)-5,7-dihydroxy-8-[4R-(3S-hydroxy-1-methyl)piperidinyl]-4H-1-benzopyran-4-one hydrochloride, crude.

To (−)-cis-2-(2-chlorophenyl)-5,7-dihydroxy-8-[4R-(3S-hydroxy-1-methyl)piperidinyl]-4H-1-benzopyran-4-one hydrochloride, crude, ethanol is added. The resulting mixture is heated to 70–79° C., stirred for 1 hour while maintaining the temperature and then filtered while still hot. The filter cake is rinsed with hot ethanol. The filtrate is concentrated by atmospheric distillation, until about 50% to about 90% of the volatiles have been removed. The remaining suspension is then cooled to 0–10° C. while isolated by filtration and dried under reduced pressure to give the ethanol solvate of (−)-cis-2-(2-chlorophenyl)-5,7-dihydroxy-8-[4R-(3S-hydroxy-1-methyl)piperidinyl]-4-H1-benzopyran-4-one hydrochloride, purified as a yellow solid.

Flavopiridol is useful in treating a number of conditions or diseases that benefit from inhibition of protein kinases, and more particularly cyclin dependent kinases as previously described herein. Flavopiridol is expected to be useful in treating a broad range of cancers including, for example, leukemia, mesothelioma and cancers of the lung (large cell, small, cell and non-small cell), colorectal, breast, ovarian, prostate melanoma, renal, uterine body and central nervous system.

All articles and patents cited herein are hereby incorporated herein by reference.

What is claimed is:

1. Anhydrous Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate having an x-ray powder diffraction pattern,

| D Space- Å |
|---|
| 12.763 |
| 6.389 |
| 3.194 |
| 13.244 |
| 4.259 | expressed in terms of D-spacing.

2. Anhydrous Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate having an x-ray powder diffraction pattern,

| D Space- Å | Relative Intensity |
|---|---|
| 12.763 | Strong |
| 6.389 | Medium |
| 3.194 | Weak |
| 13.244 | Weak |
| 4.259 | Weak |
| 12.036 | Weak |
| 2.824 | Weak |
| 8.659 | Weak |
| 6.012 | Weak |
| 5.397 | Weak |
| 3.447 | Weak | expressed in terms of D-spacing and relative intensity.

3. Anhydrous Form II (−)-cis-2-(2-chloropheyl)-5,7-dihydroxy-8-[4R-(3S-hydroxy-1-methyl)piperidinyl]-4H-1-benzopyran-4-one hydrochloride ethanol solvate having an x-ray powder diffraction pattern.

| 2 Theta Angle (°) | D Space- Å | Relative Intensity | Relative Intensity (%) |
|---|---|---|---|
| 6.920 | 12.763 | Strong | 100.0 |
| 13.850 | 6.389 | Medium | 35.7 |
| 27.908 | 3.194 | Weak | 22.2 |
| 6.669 | 13.244 | Weak | 18.0 |
| 20.838 | 4.259 | Weak | 13.8 |
| 7.339 | 12.036 | Weak | 13.8 |
| 31.660 | 2.824 | Weak | 9.5 |
| 10.208 | 8.659 | Weak | 8.3 |
| 14.722 | 6.012 | Weak | 7.2 |
| 16.413 | 5.397 | Weak | 6.9 |
| 25.829 | 3.447 | Weak | 6.5 | expressed in terms of 2 theta angle, D-spacing, relative intensity and % relative intensity.

4. A process for the preparation of anhydrous Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate comprising:
   a) dissolving a sufficient amount of (−)-cis-2-(2-chlorophenyl)-5,7-dihydroxy-8-[4R-(3S-hydroxy-1-methyl)piperidinyl]-4H-1-benzopyran-4-one hydrochloride in a sufficient amount of ethanol thus forming a mixture,
   b) heating the mixture to about 50° C. to about 80° C.,
   c) optionally filtering off undissolved material from the mixture, thus forming a solution,
   d) concentrating the solution until about 50% to about 90% of the volatiles are removed,
   e) cooling the solution and optionally isolating the obtained anhydrous (−)-cis-2-(2-chloropheyl)-5,7- dihydroxy-8-[4R-(3S-hydroxy-1-methyl)piperidinyl]-4H-1-benzopyran-4-one hydrochloride ethanol solvate crystals, and f) optionally drying the obtained crystals.

5. The process of claim 4 wherein the cooling of the solution is to about 0° C. to about 10° C.

6. Anhydrous Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate wherein said Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate is prepared by the process comprising:

a) dissolving a sufficient amount of (−)-cis-2-(2-chloropheyl)-5,7-dihydroxy-8-[4R-(3S-hydroxy-1-methyl)piperidinyl]-4H-1-benzopyran-4-one hydrochloride in a sufficient amount of ethanol thus forming a mixture, b) heating the mixture to about 50° C. to about 80° C., c) optionally filtering off undissolved material from the mixture, thus forming a solution, d) concentrating the solution until about 50% to about 90% of the volatiles are removed, e) cooling the solution and optionally isolating the obtained anhydrous (−)-cis-2-(2-chloropheyl)-5,7-dihydroxy-8-[4R-(3S-hydroxy-1-methyl)piperidinyl]-4H-1-benzopyran-4-one hydrocloride ethanol solvate crystals, and f) optionally drying the obtained crystals.

7. A pharmaceutical composition comprising a therapeutically effective amount of anhydrous Form II of (−)-cis-2-(2-chloropheyl)-5,7-dihydroxy-8-[4R-(3S-hydroxy-1-methyl)piperidinyl]-4H-1-benzopyran-4-one hydrochloride ethanol solvate and a pharmaceutically acceptable carrier.

* * * * *